United States Patent [19]

Anderson et al.

[11] Patent Number: 4,957,938

[45] Date of Patent: Sep. 18, 1990

[54] NUTRITIONAL FORMULATION FOR THE TREATMENT OF RENAL DISEASE

[75] Inventors: Pamela A. Anderson, Washington Court House; Kent L. Cipollo, Westerville; Tivadar G. Mohacsi, Columbus, all of Ohio

[73] Assignee: Abbott Laboratories, Abbott Park, Ill.

[21] Appl. No.: 369,163

[22] Filed: Jun. 21, 1989

[51] Int. Cl.$^5$ .................. A61K 31/40; A61K 37/44
[52] U.S. Cl. .................. 514/412; 514/561; 514/564; 514/567; 514/893
[58] Field of Search ............ 514/564, 567, 561, 562, 514/400, 419, 412, 893

[56] References Cited

U.S. PATENT DOCUMENTS

| | | | |
|---|---|---|---|
| 4,100,160 | 7/1978 | Walser | 514/400 |
| 4,100,161 | 7/1978 | Walser | 514/400 |
| 4,100,293 | 7/1978 | Walser | 514/562 |
| 4,296,127 | 10/1981 | Walser | 514/564 |
| 4,320,146 | 3/1982 | Walser | 514/564 |
| 4,352,814 | 10/1982 | Walser | 514/400 |
| 4,677,121 | 6/1987 | Walser et al. | 514/561 |
| 4,752,619 | 6/1988 | Walser et al. | 514/564 |

*Primary Examiner*—Douglas W. Robinson
*Assistant Examiner*—Raymond J. Henley, III
*Attorney, Agent, or Firm*—Donald O. Nickey; Edward H. Gorman, Jr.

[57] ABSTRACT

A novel nitritional formulation comprising mixtures of mixed salts formed between branched-chain α-keto-acids and basic L-amino acid is disclosed which provides optimal nutrition when consumed with a very low protein diet. The composition of this invention contains fewer components than other mixtures utilized heretofore while maintaining like proportions of the essential and semi-essential amino acids. The composition of this invention has improved thermal stability and taste and is useful for the nutritional treatment of chronic renal failure (uremia).

12 Claims, No Drawings

NUTRITIONAL FORMULATION FOR THE TREATMENT OF RENAL DISEASE

TECHNICAL FIELD

This invention relates to a composition for use in the nutritional treatment of chronic renal failure. More specifically, this invention relates to a mixture comprising four salts formed between branched-chain α-keto acids and basic L-amino acids; a salt of α-hydroxy-γ-methylthiobutyrate and three amino acids. The novel composition of this invention can be used in conjunction with a very low protein diet, a vitamin and mineral supplement and other therapeutics for the treatment of renal disease.

BACKGROUND ART

U.S. Pat. No. 4,752,619 discloses and claims a method and composition for the nutritional treatment of chronic renal failure. This reference discloses a mixture of salts which are the reaction product of a basic L-amino acid selected from the group consisting of L-ornithine, L-lysine and L-histidine and a branched-chain α-keto analog of an essential amino acid selected from the group consisting of α-ketoisocaproate, α-ketoisovalerate, and α-keto-β-methylvalerate. The '619 reference claims compositions of no more than five of said salts in recited proportions. The specification and all of the examples recited in the '619 reference relate to mixtures of five salts. The '619 reference does not disclose nor does it contemplate the use of a four salt formulation which provides unexpected product stability while maintaining the equivalent nutritional values. This reference also fails to disclose or anticipate the benefits of the instant four salt composition. These benefits include, but are not limited to lower ingredient costs, increased product stability, reduced quality control, improved odor, improved flavor and improved product homogeneity.

European patent application No. 295,166 discloses pharmaceutical compositions for the treatment of uremia which comprises keto-acid salts of ornithine, histidine and lysine. This reference fails to disclose or anticipate that a specific nutritional formulation of four keto salts would evidence enhanced thermal stability and palatability while at the same time supplying the necessary nutritional requirements to the uremic patient.

U.S. Pat. No. 4,677,121 discloses and claims a method of reducing muscle protein degradation in patients suffering from such degradation comprising administering to said patient an effective amount of a composition consisting essentially of α-ketoisocaproic acid (ketoleucine) or a pharmaceutically acceptable salt thereof. U.S. Pat. No.4,352,814 discloses and claims a composition useful for providing essential and semi-essential amino acids to the body for the treatment of renal disease in humans. The composition comprises the reaction product of the following compounds: α-ketoisovaleric acid, α-ketoisocaproic acid, α-keto-β-methylvaleric acid, histidine, threonine, and lysine. Said reaction product being formed in aqueous medium followed by removal of water. These references fail to suggest or disclose the unexpected benefits that can be realized with the specific four salt formulation of the instant invention.

U.S. Pat. No. 4,320,146 is directed to novel compounds prepared by reacting ornithine or arginine with α-keto analogs of branched chain essential amino acids namely valine, leucine and isoleucine. This reference discloses that the compounds are useful either individually or as a mixture in the treatment of hepatic disorders. The reference also suggests that the compounds of the reference have utility in the treatment of renal failure. More specifically, this reference is directed to a composition for promoting protein synthesis which comprises a carrier and an effective amount of at least one compound having the formula AK.x $H_2O$ wherein A is selected from the group consisting of arginine and ornithine; K is an α-keto analog of a branched-chain essential amino acid and x varies from 0 to about 1. This reference fails to disclose or suggest the specific formulation of the instant invention which unexpectedly possesses enhanced thermal stability and palatability.

U.S. Pat. No. 4,296,127 discloses a compound useful in the treatment of nitrogen wasting disorders and protein malnutrition which comprises a compound of the formula AN.x $H_2O$ wherein A is selected from the group consisting of essential amino acids and semi-essential amino acids, N is selected from the group consisting of α-keto and α-hydroxy analogs of essential or semi-essential amino acids, but when A is L-ornithine or L-arginine, N is not an α-keto analog of a branched chain essential amino acid, and x may be zero or a positive number which need not be an integer.

U.S. Pat. No. 4,228,099 discloses and claims compounds which are prepared by reacting ornithine or arginine with α-keto analogs of branched chain essential amino acids. The compounds disclosed in the '099 reference are useful either individually or as a mixture in the treatment of hepatic disorders and may also be useful in the treatment of renal failure.

Japanese Patent Journal No. Showa 54(1979)-117020 discloses an improved fluid useful in purifying body fluids. This reference discloses that the nitrogen balance in the body can be improved by adding a specified substance to the body fluid during its purification. The reference discloses that adding at least one type of α-keto-acid of an essential amino acid to the solution being used as a dialytic is beneficial.

U.S. Pat. No. 4,100,161 discloses and claims compositions containing keto-analogs of certain amino acids which are essential for humans and can be therapeutically employed in the treatment of patients restricted to low protein diets. The composition of the '161 reference consists of effective quantities of keto-acid analogs of the branched-chain essential amino acids valine, leucine and isoleucine. In similar fashion U.S. Pat. No. 4,100,160 discloses a composition capable of promoting protein synthesis and conserving nitrogen in a patient in need thereof. The composition of the '160 patent being in the form of a mixture adapted for oral or parenteral administration to subjects on a protein-restricted diet. The '160 composition comprising a mixture of effective quantities of hydroxy-acid or keto-acid analogs of the essential amino acids valine, phenylalanine, isoleucine, leucine and methionine. The '160 patent requires that at least one f the analogs of the essential amino acids be a hydroxy acid analog. Said hydroxy acid or keto-acid analog being present in the form of the acid analogs per se or salts of the acid analogs.

U.S. Pat. No. 4,100,293 discloses that certain compositions comprising keto-analogs of certain essential amino acids are useful in the treatment of hepatic disorders. In the preferred embodiment of this reference the composition is comprised of the keto-analogs of valine, phenylalanine, methionine, leucine, and isoleucine.

The prior art does not suggest or disclose the specific formulation of the instant invention which provides required nutritional values to the patient consuming a low protein diet while unexpectedly increasing product stability, providing improved odor and flavor while at the same time reducing the manufacturing costs and quality control costs.

Organic sats of basic L-amino acids and α-keto-analogs of branched chain essential amino acids are known to be useful in the treatment of hepatic disorders and for treatment of renal failure. Branched chain keto-acids and α-ketoisocaproate in particular are known to exhibit a protein sparing effect in patients with chronic renal failure. That is, branched chain keto-acids reduce urinary nitrogen loss. These keto-acids have been used to improve the nitrogen balance in patients suffering from a number of different nitrogen wasting conditions.

Keto acid analogs are also known to be adequate nutritional substitutes for several of the essential amino acids. Substitution of keto-analogs for essential amino acids makes possible a reduction in the nitrogen intake of uremic patients. The nitrogen sparing effect of keto-analogs has been clinically confirmed.

The medical community has long searched for an effective nutritional regimen for the treatment of chronic renal failure (pre-dialysis phase) which would maintain proper protein nutrition as well as energy balance while minimizing intake of protein containing foods which contribute to uremic toxicity. Protein restriction is believed to retard the rate of progression of chronic renal insufficiency.

Some of the prior art discussed above has attempted to optimize the nutritional treatment of chronic renal failure through a diet supplemented with calcium salts of essential amino acid keto-analogs. This approach, however, suffers from the fact that calcium salts of keto-analogs are known to be highly unpalatable and thus must be highly taken as coated granules or tablets. The medical community has also determined that the circulating concentrations of amino acids in the blood remain abnormal while on this particular regimen as they also do on supplements based on essential amino acids themselves.

A more recent approach replaces the calcium salts of keto-analogs with salts formed between branched chain α-keto-acids and basic L-amino acids. These salts have been found to be more soluble and less unpalatable than the calcium salts of the keto-acids and therefore, may be taken as a powder dissolved in water or fruit juice. It has been determined however, that long term storage of the prior art composition results in degradation of the composition. A viable product useful on a commercial scale must have prolonged stability while at the same time maintaining nutritional equivalence and hopefully improved palatability.

These prior art supplements are prepared by mixing up to 10 different constituents. The large number of constituents increases the difficulty of preparation of the supplement as well as the associated cost. Since shelf life of the mixture is limited by the storage stability of the least stable of the individual components of the mixture, mixtures of a large number of components tend to have a shorter shelf life than those with a relatively small number of constituents. Thus, it is desirable to obtain a supplement having fewer constituents and which demonstrates the same effectiveness in arresting the progression of chronic renal failure while maintaining proper nutrition.

DISCLOSURE OF THE INVENTION

There is disclosed an improved dietary supplement for use by renal patients on a low protein diet which provides the necessary amounts of essential amino acids while demonstrating enhanced palatability and thermal stability.

More specifically this invention discloses a method for nutritional treatment of renal failure comprising enteral or parenteral administration of an effective dosage to subjects suffering from this condition of a composition comprising:

(a) a mixture of salts consisting of L-ornithine-α-ketoisovalerate, L-ornithine-α-ketoisocaproate, L-lysine-α-keto-β-methylvalerate, L-histidine-α-ketoisocaproate;

(b) a calcium, sodium or potassium salt of α-hydroxy-γ-methylthiobutyrate; and (c) the amino acids L-tryptophan, L-tyrosine and L-threonine.

There is also disclosed a method for the nutritional treatment of renal failure comprising enteral or parenteral administration of an effective dosage to subjects suffering from this condition of a composition comprising:

(a) a mixture of salts consisting of L-ornithine-α-ketoisovalerate, L-ornithine-α-keto-β-methylvalerate, L-lysine-α-ketoisocaproate, L-histidine-α-ketoisocaproate;

(b) a calcium, sodium or potassium salt of α-hydroxy-γ-methylthiobutyrate; and (c) the amino acids L-tryptophan, L-tyrosine and L-threonine.

Also disclosed is a composition of matter consisting essentially of a mixture of L-ornithine-α-ketoisovalerate, L-ornithine-α-ketoisocaproate, L-lysine-α-keto-β-methylvalerate, L-histidine-α-ketoisocaproate, the calcium, sodium or potassium salt of α-hydroxy-γ-methylthiobutyrate, L-tryptophan, L-tyrosine and L-threonine.

There is also disclosed a composition of matter consisting essentially of a mixture of L-ornithine-α-ketoisovalerate, L-ornithine-α-keto-β-methylvalerate, L-lysine-α-ketoisocaproate, L-histidine-α-ketoisocaproate, the calcium, sodium or potassium salt α-hydroxy-γ-methylthiobutyrate, L-tryptophan, L-tyrosine and L-threonine.

More preferably the compositional ranges of the components are present in the following portions by weight:

| | |
|---|---|
| L-ornithine-α-ketoisovalerate | 20–25% |
| L-ornithine-α-ketoisocaproate | 20–25% |
| L-lysine-α-keto-β-methylvalerate | 20–25% |
| L-histidine-α-ketoisocaproate | 5–9% |
| calcium, sodium or potassium salt of α-hydroxy-Y-methylthiobutyrate | 1–3% |
| L-tryptophan | 0.1–1% |
| L-tyrosine | 15–20% |
| L-threonine | 3–7% |

Most preferably the composition of matter wherein the components are present in the following portions by weight:

| | |
|---|---|
| L-ornithine-α-ketoisovalerate | 21–24% |
| L-ornithine-α-ketoisocaproate | 21–24% |
| L-lysine-α-keto-β-methylvalerate | 21–24% |

| | |
|---|---|
| -continued | |
| L-histidine-α-ketoisocaproate | 6–8% |
| calcium, sodium or potassium salt of α-hydroxy-Y-methylthiobutyrate | 1.5–2.5% |
| L-tryptophan | 0.25–0.75% |
| L-tyrosine | 16–19% |
| L-threonine | 4–6% |

More preferably a composition of matter wherein the components are present in the following portions by weight:

| | |
|---|---|
| L-ornithine-α-ketoisovalerate | 20–25% |
| L-ornithine-α-keto-β-methylvalerate | 20–25% |
| L-lysine-α-ketoisocaproate | 20–25% |
| L-histidine-α-ketoisocaproate | 5–9% |
| calcium, sodium or potassium salt of α-hydroxy-Y-methylthiobutyrate | 1–3% |
| L-tryptophan | 0.1–1% |
| L-tyrosine | 15–20% |
| L-threonine | 3–7% |

Most preferably the composition of matter wherein the components are present in the following portions by weight:

| | |
|---|---|
| L-ornithine-α-ketoisovalerate | 21–24% |
| L-ornithine-α-ketoisocaproate | 21–24% |
| L-lysine-α-keto-β-methylvalerate | 21–24% |
| L-histidine-α-ketoisocaproate | 6–8% |
| calcium sodium or potassium salt of α-hydroxy-Y-methylthiobutyrate | 1.5–2.5% |
| L-tryptophan | 0.25–0.75% |
| L-tyrosine | 16–19% |
| L-threonine | 4–6% |

The instant invention as a dietary supplement is preferably administered to renal patients in conjunction with a relatively low protein diet (20–30 grams per day) optionally supplemented with vitamins and minerals.

BEST MODE FOR CARRYING OUT THE INVENTION

The organic salt portion (basic amino acid plus keto-acid) of the composition of this invention is produced by combining a basic L-amino acid selected from the group consisting of ornithine, lysine and histidine with a branched-chain α-keto-acid analog selected from the group consisting of α-ketoisovalerate, α-ketoisocaproate and α-keto-β-methylvalerate. The salts so derived are combined (preferably dry blended) with the calcium, sodium or potassium salt of α-hydroxy-gamma-methylthiobutyrate, and the amino acids L-tryptophan, L-tyrosine, and L-threonine to arrive at the composition of this invention.

The branched-chain keto-acids used to prepare the organic salts are commercially available a the calcium or the sodium salts. The methods for the production of these keto-acids are well known in the art. The free acid form may be prepared from the calcium or sodium salts by addition of excess hydrochloric acid and subsequent extraction with ether and evaporation.

The L-ornithine, L-lysine and L-histidine salts of branched-chain keto-acids are prepared by combining equimolar proportions of the amino acid as free bases with the free keto-acids, and precipitating the salts with ethanol. The preparation of these organic salts from basic amino acids and α-keto-analogs is disclosed in U.S. Patent Nos. 4,228,099 and 4,296,127 and the teachings of these patents are herein incorporated by reference.

Effective dosages of the composition of the present invention can vary according to the weight of the patient, the severity of the condition, and other factors known to the health care professional. Representative of the composition of this invention which is effective in the treatment of chronic renal failure, consists of a mixture of specific components within ranges as set forth in the following Table I.

TABLE 1

| | Compound | % by wt. |
|---|---|---|
| 1. | L-Ornithine-α-Ketoisovalerate | 20–25 |
| 2. | L-Ornithine-α-Ketoisocaproate or L-Lysine α-Ketoisocaproate | 20–25 |
| 3. | L-Lysine-α-Keto-β-Methylvalerate or L-Ornithine α-Keto-β-Methylvalerate | 20–25 |
| 4. | L-Histidine-α-Keto-Isocaproate | 5–9 |
| 5. | Calcium, Sodium or Potassium-α-Hydroxy-Y-Methylthiobutyrate | 1–3 |
| 6. | L-Tryptophan | 0.1–1 |
| 7. | L-Tyrosine | 15–20 |
| 8 | L-Threonine | 3–7 |

While the compositions of the present invention may be administered either orally or parenterally they are especially adapted for oral or enteral administration. The compositions of this invention are preferably administered by dissolving or suspending them in a fruit juice such as orange juice or they may be dissolved or suspended in water containing flavoring agents. It is preferred that the mixtures be completely dissolved or at least suspended in an aqueous medium. However, the mixtures of the invention may also be administered orally in a dry form such as tablets or capsules. The composition of this invention may also contain other dietary supplements such as vitamins and minerals.

The treatment of humans with chronic renal failure with salts of basic amino acids and α-keto-analogs of branched-chain essential amino acids has been previously documented. The composition of this invention provides about the same nutritional values as does the supplement "EE" as disclosed in U.S. Pat. No. 4,752,619 which has demonstrated clinical efficacy in the management of renal disease.

Experimental

EXAMPLE 1

To evaluate the nutritional properties of this invention a formula according to the invention (Formula A) is compared to a prior art formula which is a seven keto-acid composition and corresponds to the "EE" supplement disclosed in U.S. Pat. No. 4,752,619 (Control). The Control formula is set out in Table II and the formula according to the invention is set out in Table III.

TABLE II

| Control "EE" Control Formula | |
|---|---|
| Compound | % by wt |
| L-Ornithine α-Ketoisovalerate | 9.5 |
| L-Ornithine α-Ketoisocaproate | 10.0 |
| L-Ornithine α-Keto-β-Methylvalerate | 10.0 |
| L-Lysine α-Ketoisovalerate | 10.0 |
| L-Lysine α-Ketoisocaproate | 10.6 |
| L-Lysine α-Keto-β-Methylvalerate | 10.6 |
| L-Histidine α-Ketoisocaproate | 6.2 |
| Calcium α-Hydroxy-Y-Methylthiobutyrate | 3.7 |
| L-Tryptophan | 0.3 |
| L-Tyrosine | 19.8 |

TABLE II-continued

| Control "EE" Control Formula | |
|---|---|
| Compound | % by wt |
| L-Threonine | 9.7 |
| Total | 100.1 |

TABLE III

| Formula A.-Invention | |
|---|---|
| Compound | % |
| L-Ornithine α-Ketoisovalerate | 22.5 |
| L-Ornithine α-Ketoisocaproate | 22.2 |
| L-Lysine α-Keto-β-Methylvalerate | 23.4 |
| L-Histidine α-Ketoisocaproate | 6.9 |
| Calcium α-Hydroxy-Y-Methylthiobutyrate | 2.1 |
| L-Tryptophan | 0.3 |
| L-Tyrosine | 17.5 |
| L-Threonine | 5.1 |
| Total | 100.0 |

As discussed previously these supplements are designed to fulfill the nutritional requirements of renal patients that are consuming a low protein diet. The protein sources usually consist of bread, cereals, macaroni, broccoli and the like. These food sources many lack certain essential amino acids and thus these supplements are designed to supply those amino acids that are missing from a low protein diet.

The following Table IV sets forth the amino acid content of a low protein diet, the formulation according to this invention (Formula A), the "EE" Control, total from diet plus invention (Formula A), total from diet plus Control and adult required daily allowances. These values are expressed in millimoles/day.

chronic renal failure patients, consuming a low protein diet, are in need of such increased amounts as known from the following two articles: Alvestrand A. Furst P, Bergstrom J: Intracellular amino acids in uremia. Kidney Int 24 (supp 16): S9–S16, 1983 and Jones MR, Kopple KD: Valine metabolism in normal and chronically uremic man. Am J Clin Nutr 31:1660–1664, 1978.

The amount of α-hydroxy-γ-methylthiobutyrate has been reduced in the instant formulation to improve formula acceptance and accommodate patient tolerance to sulfur amino acids. Threonine was also reduced in the formula of this invention to improve plasma threonine concentrations which were observed to be elevated above normal when the level of intake was raised as evidenced by the following publication: Mitch WE, Abras E, Walser M: Long-term effects of a new ketoacid-amino acid supplement in patients with chronic renal failure. Kidney Int 22:48–53, 1982.

In addition, compositional changes in the lysine, ornithine and tyrosine levels as well as the addition of tryptophan were made to ensure nutritional adequacy of the instant formulation.

Table IV under the Protein Intake Diet column sets forth the intake of each amino acid from a typical diet that would be available to the patient. The nutritional values from the diet plus that provided from each ketoacid formulation (including ornithine) yields the total diet that a renal patient would receive under each regimen.

From a comparison of the amino acid contents of the Control "EE" vs. the instant invention, it is evident that the level of lysine provide by the Control "EE" is quite high and represents 16% of the ketoacid preparation, and thus, increases the total dietary lysine concentration

TABLE IV

| | | KETOACID FORMULATIONS NUTRITION EQUIVALENCY | | | | |
|---|---|---|---|---|---|---|
| AMINO ACIDS OR ANALOGUES | PROTEIN INTAKE DIET (a) MMOL/DAY | KETOACID FORMULATION (b) MMOL/DAY | | ADULT RDA (b,c) (MG/DAY) | TOTAL DIET PLUS | |
| | | Formula A | Control "EE" | | Formula A | Control "EE" |
| ISOLEUCINE (KMV)* | 8.45 | 14.0 | 14.0 | 5.85 | 22.45 | 22.45 |
| LEUCINE (KIC)* | 13.57 | 18.0 | 18.0 | 7.81 | 31.57 | 31.57 |
| VALINE (KIV)* | 10.57 | 15.0 | 14.0 | 7.64 | 25.57 | 24.57 |
| L-LYSINE | 9.07 | 14.0 | 21.0 | 5.25 | 23.07 | 30.07 |
| L-ORNITHINE | 0.00 | 29.0 | 21.0 | — | 29.00 | 21.00 |
| L-HISTIDINE | 3.54 | 4.0 | 4.00 | — | 7.54 | 7.54 |
| L-THREONINE | 7.48 | 7.0 | 14.0 | 4.3 | 14.48 | 21.48 |
| L-TRYPTOPHAN | 1.40 | 0.25 | 0.0 | 0.94 | 1.65 | 1.40 |
| L-PHENYLALANINE+ | 6.54 | 0.0 | 0.0 | 5.92 | 6.54 | 6.54 |
| L-TYROSINE | 4.56 | 16.0 | 20.0 | — | 20.56 | 24.56 |
| L-METHIONINE (OH-MET)*+ | 3.33 | 2.0 | 4.0 | 4.79 | 5.33 | 7.33 |
| L-CYSTINE | 2.87 | 0.0 | 0.0 | — | 2.87 | 2.87 |
| L-ARGININE | 7.28 | 0.0 | 0.0 | — | 7.28 | 7.28 |
| L-ALANINE | 11.45 | 0.0 | 0.0 | — | 11.45 | 11.45 |
| L-ASPARAGINE | 12.92 | 0.0 | 0.0 | — | 12.92 | 12.92 |
| L-GLUTAMIC ACID | 40.64 | 0.0 | 0.0 | — | 40.64 | 40.64 |
| L-GLYCINE | 13.24 | 0.0 | 0.0 | — | 13.24 | 13.24 |
| L-PROLINE | 16.64 | 0.0 | 0.0 | — | 16.64 | 16.64 |
| L-SERINE | 11.80 | 0.0 | 0.0 | — | 11.80 | 11.80 |
| TOTAL | 185.36 | 119.25 | 130.0 | N/A | 304.61 | 315.36 |

(a) 25 grams protein/day.
(b) Based on 64 kg body weight.
(c) Recommended Dietary Allowances, ed. 9, Washington DC. National Academy of Science, 1980.
*The amino acid or its keto-analogs: KMV = α-Keto-β-methylvalerate; KIC = α-Ketoisocaproate; KIV = α-ketoisovalerate; OH-MET = α-hydroxyY-methylthiobutyrate.
+ For purposes of RDA's L-phenylalanine is combined with L-tyrosine and L-methionine is combined with L-cystine.

From Table IV, it is apparent that the formulation, according to the present invention is designed to provide similar amounts of α-ketoisocaproate and α-keto-β-methylvalerate, but slightly more α-ketoisovalerate than the prior art "EE" control formula. This modification has been made to increase the available valine since to approximately 9.5% of total protein. Typical proteins provide a average of 6.7% lysine. See Stegink LD, Bell EF, Daabees TT et al.: Factors influencing utilization of glycine, glutamate and aspartate in clinical products, in Amino Acids: Metabolism and Medical Applications, Blackburn GL, Grant JP, Young VR, ed. John Wright, PSG Inc; Boston, 1983. pp 123-146. Typically low protein diets can provide as little as 5% lysine. Reduction of the lysine content of the instant invention has been made so not to be excessive while at the same time providing more lysine for renal patients which is nutritionally appropriate.

Since the ketoacids are supplied in part as lysine salts in this invention another basic amino acid, ornithine, had to be increased to maintain the appropriate levels of the ketoacids. The increased ornithine levels of the instant invention are more acceptable since it is desirable and a dispensable amino acid which, even at very high levels, quickly clears the blood. See Cynober L, Vaubourdolle M, Dore A, et al.: Kinetics and metabolic effects of orally administered ornithine α-ketoglutarate in healthy subjects fed with a standardized regimen. Am J Clin Nutr 39:514-519, 1984 and also Walser M, Mitch WE, Abras E: Supplements containing amino acids and keto-acids in the teatment of chronic uremia. Kidney Int 24 (supp 16): S285-S289, 1983.

The level of tyrosine was also reduced in the instant formulation based on reports of plasma tyrosine response to tyrosine intake. See Alvestrand A, Furst P, Bergstrom J: Intracellular amino acids in uremia. Kidney Int 24 (supp 16): S9-S16, 1983 and Walser M, Mitch WE, Abras E: Supplements containing amino acids and keto-acids in the teatment of chronic uremia. Kidney Int 24 (supp 16): S285-S289, 1983.

Tryptophan was included in the instant invention because of concerns that a vegetable protein diet frequently consumed by a renal failure population is not of high quality and would only be marginally adequate in tryptophan. The amount provided in the instant formulation represents approximately 25% of the recommended requirement, which is certainly adequate.

In comparison to a recognized supplemental formula for the treatment of renal failure the formula of the present invention in combination with a low protein diet will adequately meet the nutritional needs of the patients.

EXAMPLE 11

Organoleptic Quality

The most effective nutritional regimen for the treatment of chronic renal failure in the predialysis phase would be one that maintained protein nutrition as well as energy balance while minimizing the intake of those components of protein containing foods that contribute to uremic toxicity. Thus, a diet of appropriate foods that do not contain appreciable levels of components that contribute to uremic toxicity supplemented by formulas of this invention or of the prior art have been found useful. One problem associated with the prior art supplemental formula has been patient compliance unless they are encapsulated, since they are very unpalatable even when dissolved or suspended in fruit juices or artificially flavored aqueous solutions. In order to enhance patient tolerance of the formulas and thereby increase compliance it is desirable to provide supplements that are more palatable to the patient. One aspect of this invention resides in the discovery that supplements of this invention results in a product with enhanced organoleptic properties or in-short tastes better. To evaluate the taste or organoleptic properties of this invention the following control and experimental formulations were prepared:

TABLE VII

| Components | g/100 g |
|---|---|
| Organoleptic Evaluation Formulation D-Invention | |
| L-Lysine α-Keto-β-Methylvalerate | 23.41 |
| L-Ornithine α-Ketoisovalerate | 22.53 |
| L-Ornithine α-Ketoisocaproate | 22.22 |
| L-Tyrosine | 17.54 |
| L-Histidine α-Ketoisocaproate | 6.90 |
| L-Threonine | 5.05 |
| Calcium α-Hydroxy-Y-Methylthiobutyrate | 2.05 |
| L-Tryptophan | 0.30 |
| Control 5-Salt Prior Art Five Salt Formulation | |
| L-Lysine-α-Ketoisocaproate | 21.09 |
| L-Ornithine-α-Keto-β-Methylvalerate | 20.02 |
| L-Tyrosine | 19.76 |
| L-Lysine-α-Ketoisovalerate | 10.01 |
| L-Threonine | 9.74 |
| L-Ornithine-α-Ketoisovalerate | 9.47 |
| L-Histidine-α-Ketoisocaproate | 6.22 |
| Calcium-α-Hydroxy-Y-Methylthiobutyrate | 3.69 |

The prior art five salt formulation (Control 5-Salt) corresponds to the formula set out in claim 15 of U.S. Pat. No. 4,752,619. The formulations were dry blended and dissolved in tap water. 2.8 grams of the dry formula (experimental and control) were added to 104.0 gms of tap water to result in 97.4% water and 2.6% formulation by weight.

The solutions/suspensions were then evaluated for odor, flavor and after-taste by a panel of four individuals. The odor of both formulas was characterized as "skunky", "musty", "tar-like" and "fermented fruit like". These objectionable notes were more pronounced for the Control than the formulation according to this invention. In similar fashion the flavor of the Control was more objectionable in that the characteristics of "very bitter", "musty", "earthy" and "fermented fruit" where more evident than the formulation according to the present invention. The after-taste of the prior art formula lasted longer and was more objectionable than the formula of this invention.

An obvious solution to the problem of objectionable odor, taste and after taste would be to mask or flavor the solution/dispersions. The two formulas set forth in Table VII were also reconstituted with a flavor system, either orange or golden punch, to assess the flavor systems' ability to mask the objectionable organoleptic characteristics of the two formulations on a weight/weight basis. 2.8 gms of each formula from Table VII were added to 104 gms of water containing 20.0 gms of a flavoring system. The flavoring system consisted of 98.17% by weight sucrose, 1.23 wt. % citric acid and 0.60 wt. % flavor, either orange or golden punch.

Panelists evaluated the flavored formulations and it was determined that the objectionable features of the four salt formulation according to this invention were more effectively masked by the flavor system than the prior art formulation. In all evaluation categories the formulation according to the invention was superior to the flavored prior art formula. In the presence of the golden punch and orange flavor systems the objectionable qualities of the instant formulation were effectively masked, while the objectionable qualities of the prior art formulation were still pronounced. In addition, the prior art formula "flattened out" the flavor system and had a sour taste in the presence of the golden punch flavor system.

In summary, the formulation according to this invention has superior odor, flavor and after taste characteristics when compared to the prior art formulation as set forth in U.S. Pat. No. 4,752,619, when reconstituted in water without added flavors, or when reconstituted in water in the presence of orange or golden punch flavor systems.

EXAMPLE III

Thermal Stability

A dietary supplement for the treatment of renal disorders must not degrade during manufacturing and storage of the product prior to its use. It is known that prior art formulations are subject to thermal degradation and thus, limits the product's shelf life. In order to demonstrate the superior stability of the formulations according to this invention the following stability studies were conducted.

The Controls were a seven salt formulation and a four salt formulation (outside the claims). The Experiments were two 4 salt formulations. All four formulations were enrolled in an accelerated storage stability program to evaluate the stability characteristics of these dry-blended mixtures. The required components were received from Ajinomoto Chemical Company and were used as received. The formulations were prepared in a Patterson-Kelley dry-blender equipped with an intensifier bar.

The composition of each formulation is listed below.

Control-7 Salt

| Compound | % | g/2 kg |
|---|---|---|
| L-Ornithine α-Ketoisovalerate | 16.2 | 325.4 |
| L-Ornithine α-Ketoisocaproate | 14.1 | 281.2 |
| L-Ornithine α-Keto-β-Methylvalerate | 14.1 | 281.2 |
| L-Lysine α-Ketoisovalerate | 7.8 | 156.2 |
| L-Lysine α-Ketoisocaproate | 8.2 | 164.4 |
| L-Lysine α-Keto-β-Methylvalerate | 8.2 | 164.4 |
| L-Histidine α-Ketoisocaproate | 6.8 | 135.8 |
| Calcium α-Hydroxy-Y-Methylthiobutyrate | 2.0 | 40.2 |
| L-Tryptophan | 0.3 | 6.0 |
| L-Tyrosine | 17.3 | 345.4 |
| L-Threonine | 5.0 | 99.4 |
| Total | 100.0 | 1,999.6 |

Control 4 Salt

| Compound | % | g/2 kg |
|---|---|---|
| L-Ornithine α-Ketoisocaproate | 22.2 | 444.0 |
| L-Ornithine α-Keto-β-Methylvalerate | 22.2 | 444.0 |
| L-Lysine-α-Ketoisovalerate | 23.8 | 475.8 |
| L-Histidine α-Ketoisocaproate | 6.9 | 138.0 |
| Calcium α-Hydroxy-Y-Methylthiobutyrate | 2.0 | 40.8 |
| L-Tryptophan | 0.3 | 6.0 |
| L-Tyrosine | 17.5 | 350.6 |
| L-Threonine | 5.0 | 100.8 |
| Total | 99.9 | 2,000.0 |

Experimental A-4 Salt

| Compound | % | g/2 kg |
|---|---|---|
| L-Ornithine α-Ketoisovalerate | 22.5 | 450.8 |
| L-Ornithine α-Ketoisocaproate | 22.2 | 444.4 |
| L-Lysine α-Keto-β-Methylvalerate | 23.4 | 468.0 |
| L-Histidine α-Ketoisocaproate | 6.9 | 138.0 |
| Calcium α-Hydroxy-Y-Methylthiobutyrate | 2.1 | 41.0 |
| L-Tryptophan | 0.3 | 6.0 |
| L-Tyrosine | 17.5 | 350.8 |
| L-Threonine | 5.1 | 101.0 |
| Total | 100.0 | 2,000.0 |

Experimental B-4 Salt

| Compound | 25 % | 32 g/2 kg |
|---|---|---|
| L-Ornithine α-Ketoisovalerate | 22.5 | 450.8 |
| L Ornithine α-Keto-β-Methylvalerate | 22.2 | 444.4 |
| L-Lysine α-Ketoisocaproate | 23.4 | 468.0 |
| L-Histidine α-Ketoisocaproate | 6.9 | 138.0 |
| Calcium α-Hydroxy-Y-Methylhiobutyrate | 2.1 | 41.0 |
| L-Tryptophan | 0.3 | 6.0 |
| L-Tyrosine | 17.5 | 350.8 |
| L-Threonine | 5.1 | 101.0 |
| Total | 100.0 | 2,000.0 |

The prepared formula was placed in glass containers with 15 grams per bottle. The bottles were covered with aluminum foil hoods, labeled with a temperature range, storage time and other identifying information. Five different temperature ranges were used to determine the stability of the Controls and the Experimentals. These ranges were 5, 25, 37, 43 and 55 degrees Centigrade. The samples were prepared and placed in an incubator of the appropriate temperature.

Samples were withdrawn from the bottles at the noted times and were held at −20 degrees Centigrade until analyzed.

Threonine, tyrosine, histidine, ornithine and lysine contents were determined by amino acid analysis. Ketoisovaleric acid, (KIV), hydroxymethylthiobutyrate (HMTB), tryptophan (Trp), ketoisocaproate acid (KIC), and ketomethylvaleric acid (KMV) levels were quanitated by HPLC. All samples were analyzed on a weight/weight "as is basis" with no corrections made in the reported data for moisture uptake, moisture loss, residual solvent loss, and/or volatilization of degradation products that might have occurred during storage. The following tables set forth the results of this experiment for each measure of time and temperature.

Experimental error is conservatively estimated to b +/−3%, thus all component losses of 3% or less are indicated by "—" in the following Tables VIII through XIV.

TABLE VIII

PERCENT LOSS OF COMPONENT THROUGH 555 DAYS AT 5° C.

| BLEND | HIS (%) | HMTB (%) | KIC (%) | KIV (%) | KMV (%) | LYS (%) | ORN (%) | THR (%) | TRP (%) | TYR (%) |
|---|---|---|---|---|---|---|---|---|---|---|
| Exp A | — | — | — | 4.3 | 3.5 | 4.8 | 4.4 | — | — | 3.6 |
| Exp B | — | — | — | 3.4 | 3.3 | 4.2 | — | — | 6.9 | — |
| Control 7-salt | 4.5 | — | — | 4.6 | 3.3 | 5.7 | 5.5 | — | 6.8 | 4.0 |

TABLE IX

PERCENT LOSS OF COMPONENT THROUGH 250 DAYS AT 25° C.

| BLEND | HIS (%) | HMTB (%) | KIC (%) | KIV (%) | KMV (%) | LYS (%) | ORN (%) | THR (%) | TRP (%) | TYR (%) |
|---|---|---|---|---|---|---|---|---|---|---|
| Exp A | 4.1 | — | 3.7 | — | — | 3.6 | — | — | — | — |
| Exp B | 3.6 | — | 6.2 | — | — | 3.3 | — | — | — | — |
| Control 7-salt | 4.3 | — | 7.0 | — | — | 3.1 | — | — | — | — |

TABLE X

PERCENT LOSS OF COMPONENT THROUGH 75 DAYS AT 37° C.

| BLEND | HIS (%) | HMTB (%) | KIC (%) | KIV (%) | KMV (%) | LYS (%) | ORN (%) | THR (%) | TRP (%) | TYR (%) |
|---|---|---|---|---|---|---|---|---|---|---|
| Exp A | 5.0 | — | 20.8 | — | 4.5 | — | — | — | — | — |
| Exp B | 3.5 | 4.9 | 22.4 | — | — | — | — | — | — | — |
| Control 7-salt | 3.9 | 3.3 | 30.4 | — | — | — | — | — | — | — |
| Control 4-salt | 5.0 | — | 35.5 | — | — | — | — | — | — | — |

TABLE XI

PERCENT LOSS OF COMPONENT THROUGH 75 DAYS AT 43° C.

| BLEND | HIS (%) | HMTB (%) | KIC (%) | KIV (%) | KMV (%) | LYS (%) | ORN (%) | THR (%) | TRP (%) | TYR (%) |
|---|---|---|---|---|---|---|---|---|---|---|
| Exp A | — | — | 18.4 | — | 12.9 | 5.3 | — | — | — | — |
| Exp B | — | 5.9 | 25.2 | — | 7.3 | — | — | — | — | — |
| Control 7-salt | 3.9 | — | 27.8 | — | 8.2 | 3.6 | — | — | — | — |
| Control 4-salt | 6.8 | — | 35.1 | 9.0 | 6.1 | — | 3.2 | — | — | — |

TABLE XII

PERCENT LOSS OF COMPONENT THROUGH 5 DAYS AT 55° C.

| BLEND | HIS (%) | HMTB (%) | KIC (%) | KIV (%) | KMV (%) | LYS (%) | ORN (%) | THR (%) | TRP (%) | TYR (%) |
|---|---|---|---|---|---|---|---|---|---|---|
| Exp A | 3.2 | — | 9.7 | — | 7.0 | 4.8 | — | — | — | — |
| Exp B | 8.1 | 8.4 | 25.7 | 5.0 | 4.3 | 3.6 | — | — | — | — |
| Control 7-salt | 12.0 | 5.0 | 31.8 | 3.6 | — | 3.7 | — | — | — | — |
| Control 4-salt | 9.2 | 3.2 | 30.2 | 3.5 | 3.1 | — | — | — | — | — |

From this study it was determined that the stability of the ketoisocaproate salt (KIC) component was indicative of overall stability of the formulations. The following Table XIII sets forth the specific percent loss of only the ketoisocaproate component for each formulation.

TABLE XIII

PERCENT LOSS OF KIC

| TEMP °C. | DAYS | Exp A | Exp B | Control 7-salt | Control 4-salt |
|---|---|---|---|---|---|
| 25 | 75 | — | — | 3.2 | 3.5 |
| 25 | 250 | 3.7 | 6.2 | 7.0 | — |
| 37 | 75 | 20.8 | 22.4 | 30.4 | 35.5 |
| 37 | 96 | 22.6 | 23.9 | 32.9 | — |
| 43 | 75 | 18.4 | 25.2 | 27.8 | 35.1 |
| 55 | 5 | 9.7 | 25.7 | 31.8 | 30.2 |

From Table XIII it can be seen that Experimentals A and B both exhibited better stability than the Controls as indicated by percent loss of KIC. It is quite surprising that Experimental A was so much better than the 4-salt Control. It is thus apparent that simply reducing the number of keto-salts in the formulation does not result in enhanced stability.

To further demonstrate the unexpected thermal stability of formulations according to this invention Table XIV is presented as a compilation of the data contained in Tables IX–XII.

TABLE XIV

TOTAL LOSS OF ALL COMPONENTS ON A g/100 g BASIS

| TEMP °C. | DAYS | Exp A | Exp B | Control 7-salt | Control 4-salt |
|---|---|---|---|---|---|
| 55 | 5 | 2.86 | 5.55 | 5.85 | 5.40 |
| 43 | 40 | 2.27 | 3.09 | 3.38 | 4.84 |
| 37 | 48 | 1.81 | 2.13 | 3.19 | 3.72 |
| 25 | 250 | 1.12 | 1.42 | 1.54 | N/A |

From Table XIV it is quite apparent that Experimental A, (according to the present invention) is surprisingly superior to both the 4 and 7 salt Control formulations.

INDUSTRIAL APPLICABILITY

The most effective nutritional regimen for the treatment of chronic renal failure in the predialysis phase would be one that maintained protein nutrition while minimizing the intake of components of protein-containing foods that contribute to uremic toxicity. The medical community has for some time utilized special diets supplemented with amino acids and keto-acids in the dietary management of renal patients. The prior art supplements have the limitations of poor thermal stability and unpleasant taste. The medical community has searched for an amino acid/keto-acid supplement formulation that overcomes these limitations.

The instant invention now provides a formulation that meets the special dietary needs of renal patients while at the same time providing enhanced thermal stability and organoleptic properties. In addition, the four salt formulations of this invention are superior to the prior art 5 and 7 salt formulation since they inherently will possess lower ingredient costs, require less quality control and have improved product homogeneity.

The present invention may be embodied in other specific forms without departing from the spirit or essential attributes thereof, and accordingly reference should be made to the appended claims, rather than to the foregoing specification, as indicating the scope of the invention.

We claim:

1. A composition of matter consisting of a mixture of the following components at the following percentages by weight:

| | |
|---|---|
| L-ornithine-α-ketoisovalerate | 21–24% |
| L-ornithine-α-ketoisocaproate | 21–24% |
| L-lysine-α-keto-β-methylvalerate | 21–24% |
| L-histidine-α-ketoisocaproate | 6–8% |
| calcium, sodium or potassium salt of α-hydroxy-γ-methylthiobutyrate | 1.5–2.5% |
| L-tryptophan | 0.2–0.75% |
| L-tyrosine | 16–19% |
| L-threonine | 4–6%. |

2. A composition of matter consisting of a mixture of the following components at the following percentages by weight:

| | |
|---|---|
| L-ornithine-α-ketoisovalerate | 21–24% |
| L-ornithine-α-keto-β-methylvalerate | 21–24% |
| L-lysine-α-ketoisocaproate | 21–24% |
| L-histidine-α-ketoisocaproate | 6–8% |
| calcium, sodium or potassium salt of α-hydroxy-Y-methylthiobutyrate | 1.5–2.5% |
| L-tryptophan | 0.2–0.75% |
| L-tyrosine | 16–19% |
| L-threonine | 4–6% |

3. A method for the nutritional treatment of a subject suffering from renal failure comprising enterally or parenterally administering an effective nutritional dosage to subjects suffering from this condition a composition which consists essentially of the following components at the following percentages by weight:

| | |
|---|---|
| L-ornithine-α-ketoisovalerate | 20–25% |
| L-ornithine-α-ketoisocaproate | 20–25% |
| L-lysine-α-keto-β-methylvalerate | 20–25% |
| L-histidine-α-ketoisocaproate | 5–9% |
| calcium, sodium or potassium salt of α-hydroxy-Y-methylthiobutyrate | 1–3% |
| L-tryptophan | 0.1–1% |
| L-tyrosine | 15–20% |
| L-threonine | 3–7% |

4. The method according to claim 3 wherein the composition is administered in conjunction with a low protein diet.

5. The method according to claim 3 wherein the composition is dissolved or suspended in an aqueous media prior to administration.

6. The method according to claim 3 wherein the composition is dissolved or suspended in an aqueous media containing flavoring agents prior to administration.

7. The method according to claim 3 wherein the composition is dissolved or suspended in a fruit juice prior to administration.

8. A method for the nutritional treatment of a subject suffering from renal failure comprising enterally or parenterally administering an effective nutritional dosage to subjects suffering from this condition a composition which consists essentially of the following components at the following percentages by weight:

| | |
|---|---|
| L-ornithine-α-ketoisovalerate | 20–25% |
| L-ornithine-α-keto-β-methylvalerate | 20–25% |
| L-lysine-α-ketoisocaproate | 20–25% |
| L-histidine-α-ketoisocaproate | 5–9% |
| calcium, sodium or potassium salt of α-hydroxy-Y-methylthiobutyrate | 1–3% |
| L-tryptophan | 0.1–1% |
| L-tyrosine | 15–20% |
| L-threonine | 3–7% |

9. The method according to claim 8 wherein the composition is administered in conjunction with a low protein diet.

10. The method according to claim 8 wherein the composition is dissolved or suspended in an aqueous media prior to administration.

11. The method according to claim 8 wherein the composition is dissolved or suspended in an aqueous media containing flavoring agents prior to administration.

12. The method according to claim 8 wherein the composition is dissolved or suspended in a fruit juice prior to administration.

* * * * *